United States Patent [19]
Simon

[11] Patent Number: 6,071,121
[45] Date of Patent: Jun. 6, 2000

[54] INTRAORAL SEMI-CUSTOM BITE FORMING AND DISCLUDER DEVICE

[76] Inventor: Jerome Michael Simon, 1294 Rockrimmon Rd., Stamford, Conn. 06903

[21] Appl. No.: 09/219,049

[22] Filed: Dec. 23, 1998

[51] Int. Cl.[7] .................................................. A61C 9/00
[52] U.S. Cl. .............................................................. 433/37
[58] Field of Search ......................... 433/6, 39, 37, 433/215; 128/861, 862

[56] References Cited

U.S. PATENT DOCUMENTS

| | | | |
|---|---|---|---|
| 2,694,397 | 11/1954 | Herms | 128/861 |
| 2,705,492 | 4/1955 | Chandler | 128/862 |
| 3,124,129 | 3/1964 | Grossberg | 128/862 |
| 3,247,844 | 4/1966 | Berghash | 128/862 |
| 3,303,844 | 2/1967 | Johnson et al. | 433/6 |
| 3,864,832 | 2/1975 | Carlson | 128/862 |
| 4,419,992 | 12/1983 | Chorbajian | 433/215 |
| 4,773,853 | 9/1988 | Kussick | 433/6 |
| 4,799,500 | 1/1989 | Newbury | 128/859 |
| 4,920,984 | 5/1990 | Furumichi et al. | 433/6 |
| 4,977,905 | 12/1990 | Kittelsen et al. | 128/861 |
| 5,033,480 | 7/1991 | Wiley et al. | 128/861 |
| 5,277,203 | 1/1994 | Hays | 128/861 |
| 5,460,527 | 10/1995 | Kittelsen | 433/215 |
| 5,513,656 | 5/1996 | Boyd, Sr. | 128/859 |
| 5,795,150 | 8/1998 | Boyd | 433/6 |

*Primary Examiner*—John J. Wilson
*Attorney, Agent, or Firm*—Gregory F. Cotterell

[57] ABSTRACT

The present invention discloses an intraoral semi-custom disclusion device for use on at least one anterior upper incisor, the kit comprises a channel, adapted to removably receive within the channel the at least one upper anterior incisor. The channel has a front wall and a back wall with each generally parallel to a common plane and a floor connecting the front and back walls having a lower outer surface in a plane that is either tiltable, or tilted, to the common plane. The device also includes a curable polymeric resin for filling at least a portion of the channel. The polymeric resin is moldable around the at least one anterior upper incisor when the channel is positioned for use and is curable to a soft resilient molded shape of the at least one anterior upper incisor.

20 Claims, 2 Drawing Sheets

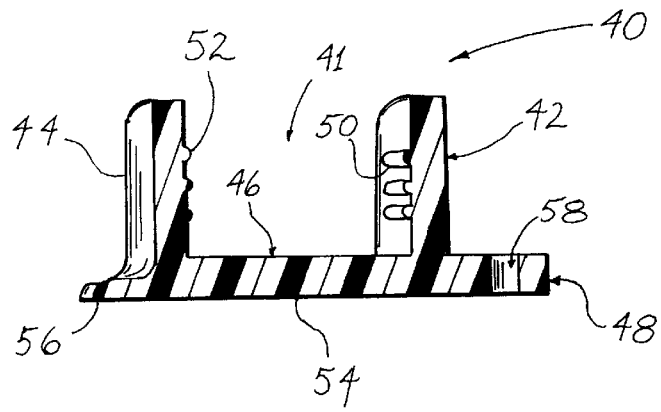
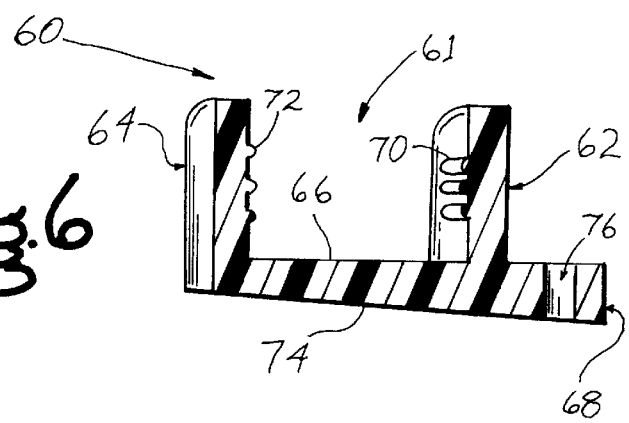
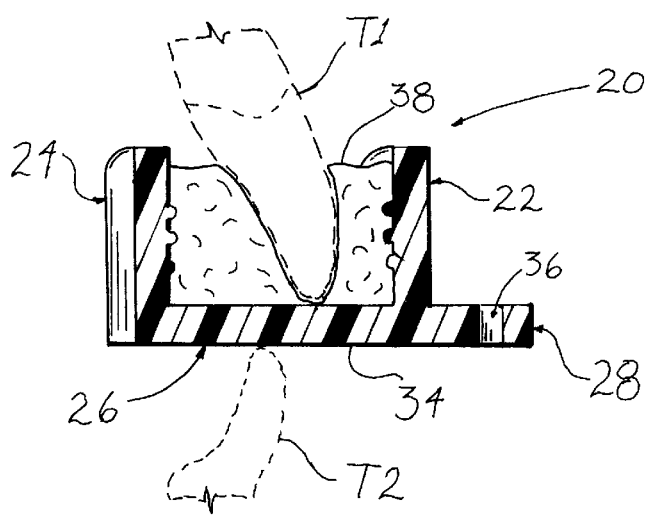

INTRAORAL SEMI-CUSTOM BITE FORMING AND DISCLUDER DEVICE

BACKGROUND OF THE INVENTION

1. Field of the Invention

The present invention relates in general to devices for the treatment of temporomandibular joint dysfunction and associated headaches, neck aches and jaw pain and, in particular, to an intraoral semi-custom bite forming and discluder device.

2. Description of the Background Art

Headache is considered one of the most frequent complaints found during a review of systems examination in doctors' offices, and the most frequent reason for use of over-the-counter medications. There are a number of causes for headache, which may be classified generally into several categories, muscular or tension, vascular, connective tissue, and infection. The source of the headache may be found intracranial, extracranial, or even have started in the upper back or neck and progressed to encompass the head secondarily.

One source for headache has recently been described as temporomandibular joint (TMJ) dysfunction. This particular dysfunction has been one of the most perplexing problems in medicine or dentistry for many years. Contributing to the confusion and misunderstanding surrounding TMJ dysfunction is the inability of professionals to agree on a definition for TMJ dysfunction. Agreement has been difficult because diagnosis and treatment for headache, neck pain, and the temporomandibular joint falls under the purview of many different medical and dental specialists, each specialty fostering their own notion of pathophysiology and its concomitant treatment.

For the purpose of this disclosure, TMJ dysfunction is defined as a constellation of pain symptoms in the head, neck, jaw or back that is combined with dental problems, such as worn, broken or loosened teeth caused by tooth clenching and or grinding. The dental problems are due to an imbalance between the occlusive (biting) surfaces of the teeth and the temporomandibular joints. This imbalance is manifest when the occlusive surfaces of the teeth, in order to fully interdigitate, force one or both of the temporomandibular joints to move out of its centered position in the socket of the joint. Therefore, if a patient has pain and or dental symptoms but does not have a conflict between the occlusive surfaces of the their teeth and the temporomandibular joints, they do not have TMJ dysfunction.

The occlusive surfaces of the teeth can only completely fit together in one position, i.e., there is only one position of maximum interdigitation. The inclined planes of the occlusive surfaces of the teeth, in fact, form a very powerful mechanical system that is capable of exerting significant mechanical advantage.

Each time the teeth are brought together all of the way, the occlusive surfaces interdigitate. The pressure applied by the teeth against each other at these surfaces literally pulls the temporomandibular joints into whatever position is required to allow the teeth to interdigitate to their maximum ability. The occlusive surfaces of the various teeth are not symmetric, therefore, for maximum interdigitation to occur across asymmetric surfaces, the muscles of the jaw must contract asynchronously to place the temporomandibular joints in whatever position the teeth force them into. This process is repeated every time one swallows or bites completely through food, over two thousand times a day.

This asymmetric positioning places strain on the jaw positioning muscles, particularly the lateral pterygoid muscles. The imbalance over time can lead to cramping and soreness in these muscles, which can be a source of head, neck, and facial pain.

A compensation mechanism for this irritation is the initiation of an "erasure" pattern of tooth clenching and grinding. This is a behavior undertaken by many people as a subliminal attempt to literally grind down or break off the offending tooth points and inclines that are causing the asymmetric jaw positioning. This erasure pattern of tooth clenching and grinding changes the entire dynamics. Now, not just the smaller positioning muscles are over contracting, but the larger muscles of the jaw, such as the temporalis, the masseter, and external pterygoids are brought into play to accomplish the grinding and clenching. This degree of intense muscle activity can cause sever cramping and pain in all of the jaw muscles, as well as, damage to the teeth, the mandible and the temporomandibular joints. In addition, this muscle activity is a causative factor in producing headache secondary the TMJ dysfunction.

Eliminating the malocclusion, centering the jaw and allowing the temporomandibular joints to seat properly is the key to relaxing the musculature and alleviating the pain associated with TMJ dysfunction. However, it is expensive and time consuming to correct the malocclusion. Orthodontia, tooth extraction and modifying tooth surface contact requires a specialist to assess the patient's condition and undertake a program that may take several years to effect adequate change in occlusion to provide for proper occlusive alignment. Several devices have been developed as temporary or interim devices in attempt to provide some relief of a more immediate nature than waiting years for slow changes to occur Example of such devices may be seen in U.S. Pat. Nos. 5,513,656 and 5,795,150, both issued to Boyd. The devices disclosed are semi-custom intraoral discluders that are placed over the anterior upper incisors. The devices make use of a trough, a soft curable material within which to imbed the incisors, and a dome on the trough extending distally into the user's mouth when in position. The dome is intended to have at least one lower incisor come to rest against the dome. However, the dome does not prevent the jaw from sliding to one side or the other and does not encourage the jaw to assume a more comfortable anatomic position of the condyles seated in the joint. This inability to center the jaw only perpetuates the imbalance in the musculature that is already present and cause of the pain. Furthermore, the dome projects into the oral cavity displacing the user's tongue, a distraction at the least that may become more of an irritant as time progresses.

What is needed is an inexpensive device that may be placed in the mouth over at least one anterior upper incisor that promotes centering of the lower jaw and proper seating of the mandibular condyles within the temporomandibular joint. The device should be easy to set up and use by the wearer, not requiring custom fitting or other expensive services from dentists, orthodontists, and the like device.

SUMMARY OF THE INVENTION

The TMJ comprises the heads of the mandibular condyles and the fossa of the joint socket of the temporalis bone. In addition, there is a disc pad of articular cartilage spaced between the head of the condyle and the fossa. For proper function and positioning, the condyle-disc assembly, specifically the medial pole, must be allowed to brace against the bony walls of the eminentia. The only position where this is possible is when the head of the condyle is in the apex of a triangle that is at the rear most, upper most, and mid most position in the fossa, to be referred to as the RUM position. This RUM position is the position that the condyles would like to assume with normal muscle pressure if the occlusive surfaces of the teeth do not force them to deviate in order for the teeth to fit together with maximum contact. With malocclusion, the heads of the condyles are forced out of the ideal RUM position. In order to avoid stress and muscle spasm, and consequently avoid severe damage to the teeth, occlusion of the teeth should not force the head of the condyles to assume a malposition within the fossa of the TMJ joint socket.

The present invention discloses an intraoral semi-custom disclusion device for use on at least one of the upper anterior incisors of a human. The device comprises a channel that is adapted to removably receive therein the at least one upper anterior incisor. The channel has a front wall and a back wall joined by a floor that has a lower outer surface. The floor is tiltable in relation to a plane that is generally perpendicular to a long axis of the at least one upper incisor. The floor is tilted by at least one lower anterior incisor contacting the lower outer surface the at least one upper anterior incisor is received within the channel.

The device further comprises a polymeric resin filling at least a portion of the channel. The polymeric resin is adapted to initially mold around the at least one anterior upper incisor and then cure to a removable soft resilient molded shape of the at least one anterior upper incisor. This shape is retained for removably receiving the at least one anterior upper incisor at the angle of tilt set by the contact of the at least one lower incisor with the lower surface.

Another embodiment of the present invention discloses an intraoral semi-custom disclusion device for use on at least one anterior upper incisor comprising a channel adapted to removably receive therein the at least one upper anterior incisor. The channel includes a front wall and a back wall with each generally parallel to a common plane and a floor connecting the front and back walls having a lower outer surface in a plane tilted to the common plane.

This embodiment further comprises a polymeric resin filling at least a portion of the channel that is adapted to mold around the at least one anterior upper incisor. The polymeric resin is curable to a removable soft resilient molded shape of the at least one anterior upper incisor.

A further embodiment of the present invention discloses an intraoral semi-custom disclusion device for use on at least one anterior upper incisor comprising a channel adapted to removably receive therein the at least one upper anterior incisor. The channel includes a front wall and a back wall with each generally parallel to a common plane and a floor connecting the front and back walls having a lower outer surface having a surface plane conforming to a segment of a frusto-conical plane tilted to the common plane.

This embodiment further comprises a polymeric resin filling at least a portion of the channel that is adapted to mold around the at least one anterior upper incisor. The polymeric resin is curable to a removable soft resilient molded shape of the at least one anterior upper incisor.

The device of the present invention is designed to solve the problem of malpositioning of the heads of the condyles within the fossa of the TMJ by providing a tilted or inclined lower surface as a functional incisor plane. The device of the present invention provides for at least one lower incisor to contact the lower surface before any other occlusive surface meets. Further, the lower surface tilt encourages centering of the lower jaw in three planes, anterior to posterior, medial to lateral, and superior to inferior movement of the jaw. This positional relationship creates a class II lever with the fulcrum located at the point of contact of the at least one lower incisor with the lower surface of the device of the present invention. The force generated by the musculature on the mandible through this class II lever allows the heads of the condyles to properly seat within the fossa at the RUM position. Once the condylar heads are in the RUM position the irritation of malpositioning of the condylar heads is removed and the muscles begin to relax.

An object of the present invention is to provide a discluder device that is semi-custom, yet is easy for anyone with little or no training to set up and use. The present invention anticipates the use of plastics and metals known to have little to no toxic effects and are comfortable to the wearer. The discluder device may have a standard one size fits all, but additional sizing is contemplated for less optimal circumstances. An example is the addition of a posterior rim extension useful for persons with a greater than usual under bite.

Another object of the present invention is to provide a device capable of contributing to the diagnostic acumen of the dental and medical practitioner. The device of the present invention provides for the proper positioning of the condyles within the joint fossa. Patients experiencing pain and headache of unknown origin may use the device of the present invention to determine relative easily and cheaply whether the pain they are experiencing is caused by TMJ disorder.

These and other objects of the present invention and many of the attendant advantages of the present invention will be readily appreciated as the same become better understood by reference to the following detailed description when considered in connection with the accompanying drawings.

BRIEF DESCRIPTION OF THE DRAWING

FIG. 4 is a side elevational cross-sectional view of the embodiment depicted in FIG. 1 depicting the use of an embedding medium with a wearer's teeth shown in phantom;

FIG. 5 is a side elevational cross-sectional view of an additional embodiment of the present invention; and FIG. 6 is a side elevational cross-sectional view of another embodiment of the present invention.

DETAILED DESCRIPTION OF THE INVENTION

Figure 1:
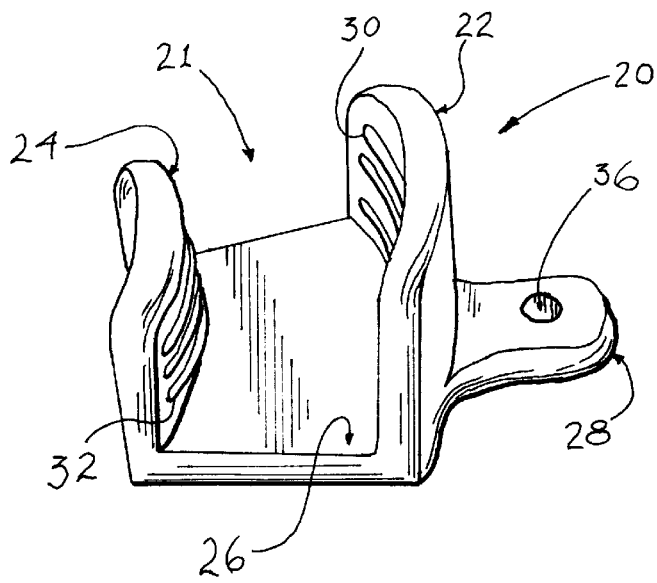
FIG. 1 is a top side perspective view of an embodiment of the present invention.
Figure 2:
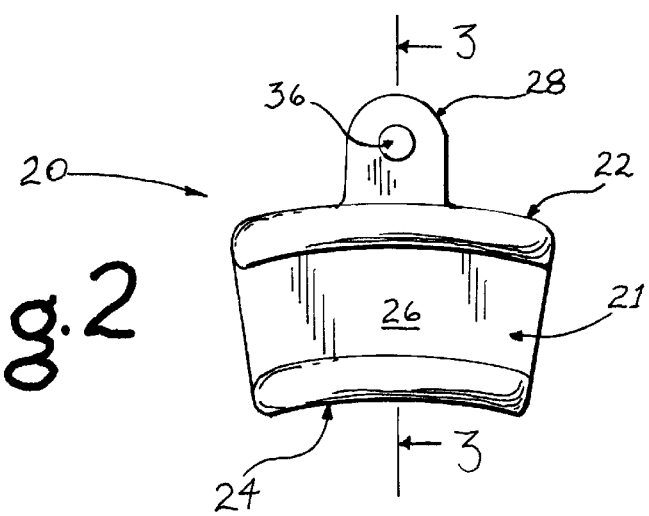
FIG. 2 is a top plan view of the embodiment depicted in FIG. 1.
Figure 3:
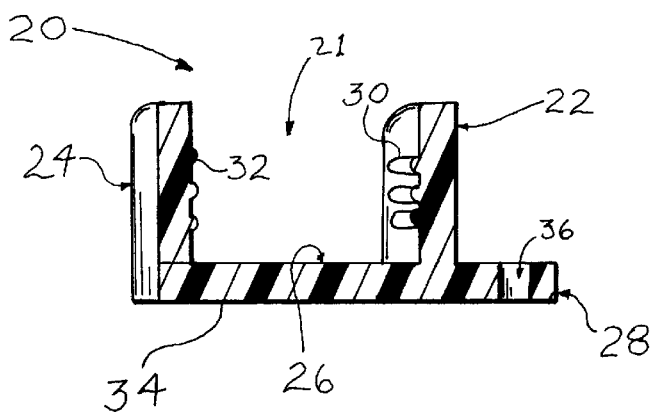
FIG. 3 is a side elevational cross-sectional view of the embodiment depicted in FIG. 2 taken along the line 3—3.

In reference to the various Figures, wherein like reference numbers refer to like components throughout the various Figures, there is disclosed an embodiment of the present invention as depicted in FIGS. 1 through 4 as a discluder device 20 including a front wall 22, a back wall 24, and a floor 26, together forming a channel 21, which further includes a tab 28. Discluder device 20 further includes a resilient polymer 38.

Front wall 22 includes ribs 30 facing the inside of channel 21. Back wall 24 includes ribs 32, also facing the inside of the channel. Floor 24 includes an under surface 34. Tab 28 includes a tab hole useful for attaching a securing strap (not shown).

Channel 21, with tab 28, may be formed as an integrated single piece. The manufacturing may involve casting a structure from a mold using various polymeric resins that may be curable or either thermosetting. Alternatively, channel 21 may be shaped from a sheet of moldable thermoplastic polymeric material. The material of choice for use as channel 21 is not limited to polymers, numerous metals, metal alloys such as stainless steel, and ceramics are also useful with discluder device 20.

For manufacturing channel 21, the present invention anticipates the use of numerous different polymeric compounds, both natural and synthetic. Polymeric compounds useful in the present invention include polyvinyl chloride, polybutylene, polyethylene, polypropylene, polystyrene, polyurethane, acrylates, methyl acrylates, cellulose and natural rubbers, and many copolymer combinations of these polymers. This list is by no means exhaustive, any polymer or copolymer with negligible or no toxicity is useful in the present invention. Preferably, the polymeric material used should cure or set to a reasonably rigid structure that will only minimally deform under reasonable stress or strain from biting by a wearer.

Resilient polymer 38 is preferably a material that is initially fluid enough to mold adequately about a wearer's dentition and then curable to a soft resiliency while maintaining the molded shape. The resilient polymer should have favorable release characteristics to provide for a mold that is removable from and replaceable to the dentition of the wearer. There are many suitable resilient curable polymeric compounds available in the dentistry profession. Examples are polyvinyl chloride and polyvinyl siloxane. A particular custom liner material useful in dental impressions is the polyvinyl siloxane impression material Jeneric Pentron Correct UPS from Jeneric Pentron, Inc., 53 North Plains Industrial Road, Wallingford, Conn. This material comes as two separate compounds, a base and an accelerator. When ready to embed, roughly equal parts of filler and accelerator are mixed until of a uniform color and then the impression is taken. The polymer cures to a soft resiliency within minutes.

Another embodiment of the present invention is depicted in FIG. 5 as a discluder device 40 including a front wall 42, a back wall 44, and a floor 46, together forming a channel 41, which further includes a tab 48. A resilient polymer has been left out intentionally, but is part of this embodiment as well.

Front wall 42 includes ribs 50 facing the inside of channel 41. Back wall 44 includes ribs 52, also facing the inside of channel 41. Floor 46 includes an under surface 54 and a posterior lip 56 running the width of discluder device 40 roughly the length of back wall 44. Lip 56 extends under surface 54 of floor 46 past back wall 44. Tab 48 includes a tab hole 58 useful for attaching a securing strap (not shown).

The addition of posterior lip 56 extends the usefulness of the present embodiment by providing for a device that is adaptable for persons that have a substantial under bite or do not have a lower incisor near their jaw's midline.

An additional embodiment of the present invention is depicted in FIG. 6 as a discluder device 60 including a front wall 62, a back wall 64, and a floor 66, together forming a channel 61, which further includes a tab 68. As with the previous embodiment, a resilient polymer has been left out intentionally, but is part of this embodiment as well.

Front wall 62 includes ribs 70 facing the inside of channel 61. Back wall 64 includes ribs 72, also facing the inside of channel 61. Floor 66 includes a tilted under surface 74, such that floor 66 is thicker anteriorly than posteriorly. Tab 68 includes a tab hole 76 useful for attaching a securing strap (not shown). Although not shown together, the embodiment of FIG. 6 may also include a posterior lip similar to posterior lip 56 shown in FIG. 5.

The tilting of under surface 74 by manufacturing the floor with a tilt in place obviates the necessity for tilting the device during the initial installation and embedding procedure. A preformed tilted under surface to a floor that does not require tilting when first placed provides for a wider opening of the jaw at the point of contact between a lower incisor and the under surface. This is useful for those persons that may have one or more high spots on their occlusive surfaces of the more rearward teeth, the bicuspids and molars. The high spot may well be the cause of their discomfort by malpositioning the lower jaw and preventing adequate closure of the mouth. A device of the present invention having a posterior lip and a tilted undersurface provides for a person to use the smallest overall device relative to the size of the person's mouth and upper anterior incisors.

In addition, the present invention also anticipates the use of a flat to a segment of a shallow frusto-conical shape for the under surface of the floor (a flat surface has been depicted in the various Figures). The use of a flat or shallow frusto-conical shape provides for ease of lateral jaw motion when at least one lower incisor contacts the under surface of a device of the present invention. The tilting of the device, or use of a tilted under surface promotes centering of the jaw on contact of at least one lower incisor with the under surface of the device, a lateral motion when the jaw is out of alignment. A shallow frusto-conical shape to the under surface contributes to the centering tendency. The tilt is not so extreme as to prevent or discourage forward and backward movement of the jaw, however, with the tilting effect, the jaw is encouraged to move posteriorly into the RUM position when at least one lower anterior incisor contacts the under surface of the device of the present invention.

An additional embodiment of the present invention anticipates the use of an attachable spacer (not shown) positionable on the under surface, such as under surface 34. The attachable spacer has several advantages. The attachable spacer may be used to increase the thickness of the floor, which increases the opening of the wearer's mouth. This is useful for those few people that may have posterior teeth that are exceptionally high and make early and inappropriate occlusive contact. In addition, the attachable surface may be contoured to alter the contour of the lower surface of a device of the present invention. In this fashion, a flat surface may be converted to a shallow frusto-conical surface and vice versa. Alternatively, a wedged shaped attachable spacer may be used to change from a tiltable floor to a more tilted floor.

The attachable spacer would be generally the same surface area as the under surface it is to attach to. Preferably, the attachable spacer is constructed with a suitable biocompatible polymer, such as polyethylene, polypropylene, polytetrafluoroethylene, polyurethane, and polyvinyl chloride. The attachable spacer may be attached using any number of different adhesives, preferably non-toxic and suitable for use in a wearer's mouth.

In use, a wearer sets up the initial wearing of the discluder device 20 of the present invention by attaching a safety strap (not shown) to tab 28 using tab hole 36 and mixing proper proportions of the filler and accelerator for curable resilient polymer 38. When thoroughly mixed, resilient polymer 38 is placed in channel 21 and discluder device 20 is then placed over at least one upper anterior incisor T1, as depicted in FIG. 4. Before resilient polymer 38 cures, the wearer closes their jaw until at least one lower anterior incisor T2 contacts under surface 34. This contact is then used to tilt discluder device 20 in relation to a generally longitudinal axis of the at least one upper anterior incisor T1. This tilting is evident by a movement of the posterior end of discluder device 20 tilting upward, or superiorly in relation to the wearer. A device of the present invention using a tilted under surface, as depicted in FIG. 6, requires less tilting, if any, at this step.

Resilient polymer 38 is allowed to cure forming an impression of the at least one upper anterior incisor T1. Discluder device 20 may now be worn until ready to be removed. The impression of anterior incisor T1 is maintained in resilient polymer 38 after removal. The impression ensures that discluder device 20 is easily repositioned in the same orientation the next time it is needed by the wearer and holds it in place on the one or more teeth when in use.

The foregoing description is considered as illustrative only of the principles of the invention, and since numerous modifications and changes will readily occur to those skilled in the art, it is not the inventor's desire to limit the invention to the exact construction and operation shown and described herein. Accordingly, all suitable modifications and equivalents may be resorted to, falling within the scope of the present invention.

I claim:

1. An intraoral semi-custom disclusion device for use on at least one upper anterior incisor of a human, the device comprising:
   a channel, including means for removably receiving therein the at least one upper anterior incisor, having a front wall and a back wall joined by a floor having an inner surface for contacting the at least one upper anterior incisor and a lower outer surface tilted at an acute angle in relation to the inner surface; and
   a polymer filling at least a portion of the channel, moldable around the at least one anterior upper incisor and curable to a resilient molded shape of the at least one anterior upper incisor when removably receiving the at least one anterior upper incisor.

2. The device of claim 1 in which the channel is constructed with a synthetic polymeric material.

3. The device of claim 2 in which the synthetic polymeric material is selected from a list consisting of: polypropylene, polyurethane, polyvinyl chloride, polyethylene, polybutylene, and polystyrene.

4. The device of claim 1 in which the channel is formed from a thermoplastic synthetic polymeric sheet.

5. The device of claim 1 in which the curable polymeric resin is selected from a list of consisting of: silicone, acrylic, polyvinyl chloride, and polyurethane.

6. The device of claim 1 further comprising a spacer adapted for placement on the lower outer surface.

7. The device of claim 6 in which the spacer includes an extension in the same plane as the lower outer surface extending outward from the back wall.

8. The device of claim 1 in which the floor includes an extension extending the surface of the lower outer surface beyond the back wall.

9. An intraoral semi-custom disclusion device for use on at least one anterior upper incisor, the device comprising;
   a channel for removably receiving therein the at least one upper anterior incisor having a front wall and a back wall with each generally parallel to a common plane and a floor connecting the front and back walls having a lower outer frusto-conical surface tilted at an acute angle to the common plane; and
   a polymeric resin filling at least a portion of the channel, moldable around the at least one anterior upper incisor and curable to a resilient molded shape of the at least one anterior upper incisor when removably receiving the at least one anterior upper incisor.

10. The device of claim 9 in which the channel is constructed with a synthetic polymeric material.

11. The device of claim 10 in which the synthetic polymeric material is selected from a list consisting of: polypropylene, polyurethane, polyvinyl chloride, polyethylene, polybutylene, and polystyrene.

12. The device of claim 9 in which the channel is formed from a thermoplastic synthetic polymeric sheet.

13. The device of claim 9 in which the curable polymeric resin is selected from a list of consisting of: silicone, acrylic, polyvinyl chloride, and polyurethane.

14. The device of claim 9 further comprising a spacer adapted for placement on the lower outer surface.

15. A method for using an intraoral semi-custom disclusion device on at least one anterior upper incisor, the method comprising the steps of;
   providing a device including a channel having a front wall and a back wall and a floor connecting the front and back walls having a lower outer surface;
   providing a curable polymeric resin for filling at least a portion of the channel, moldable around the at least one anterior upper incisor when the channel is positioned for use and curable to a resilient molded shape of the at least one anterior upper incisor when removably receiving the at least one anterior upper incisor;
   filling the channel with the curable resin;
   positioning the device over the at least one anterior upper incisor with the plane of the lower outer surface in a first position; and
   tilting the device to a second position at an acute angle to the first position.

16. The method of claim 15 in which the channel is constructed with a synthetic polymeric material.

17. The method of claim 16 in which the synthetic polymeric material is selected from a list consisting of: polypropylene, polyurethane, polyvinyl chloride, polyethylene, polybutylene, and polystyrene.

18. The method of claim 15 in which the channel is formed from a thermoplastic synthetic polymeric sheet.

19. The method of claim 15 in which the curable polymeric resin is selected from a list of consisting of: silicone, acrylic, polyvinyl chloride, and polyurethane.

20. The method of claim 15 further comprising a spacer adapted for placement on the lower outer surface.

* * * * *